US006221350B1

(12) United States Patent
Brown et al.

(10) Patent No.: US 6,221,350 B1
(45) Date of Patent: Apr. 24, 2001

(54) ENHANCEMENT OF MICROBIAL COLONISATION OF THE GASTROINTESTINAL TRACT

(75) Inventors: Ian L. Brown, Tamworth; Patricia Lynne Conway, La Perouse; David Lloyd Topping, Glenelg North; Xin Wang, Randwick, all of (AU)

(73) Assignees: The University of New South Wales, Kensington; Burns Philp & Company Limited; Burns Philp Research & Development PTY LTD, both of Sydney; The Commonwealth of Australia Commonwealth Scientific and Industrial Research Organization, Campbell; Arnott's Biscuits Limited, Homebush; Gist-Brocades Australia PTY Limited, Moorebank; Goodman Fielder Ingredients Limited, Gladesville, all of (AU)

( * ) Notice: Subject to any disclaimer, the term of this patent is extended or adjusted under 35 U.S.C. 154(b) by 0 days.

(21) Appl. No.: 09/155,117
(22) PCT Filed: Mar. 20, 1997
(86) PCT No.: PCT/AU97/00176
§ 371 Date: Apr. 12, 1999
§ 102(e) Date: Apr. 12, 1999
(87) PCT Pub. No.: WO97/34615
PCT Pub. Date: Sep. 25, 1997

(30) Foreign Application Priority Data

Mar. 20, 1996 (AU) .................................................. PN8813

(51) Int. Cl.⁷ ....................................................... A01N 63/00
(52) U.S. Cl. ..................... 424/93.3; 424/93.4; 424/93.45; 574/23; 574/24; 574/25
(58) Field of Search ................................. 424/93.3, 93.4, 424/93.45; 514/23, 24, 25

(56) References Cited

U.S. PATENT DOCUMENTS 5,147,668    9/1992    Munk ..................................... 426/61

FOREIGN PATENT DOCUMENTS

21247/67    11/1968    (AU) .
8-310960    11/1996    (JP) .
96/08261    3/1996    (WO) .

OTHER PUBLICATIONS

Nutrition Reports International, vol. 15, No. 2, Feb. 1977, Bruns et al., "Effect of Modified Starch on the Microflora of the Small Intestine and Caecum of Rats", pp. 131–138.

*Primary Examiner*—Jean C. Witz
(74) *Attorney, Agent, or Firm*—McDermott, Will & Emery

(57) ABSTRACT

Probiotic composition comprising one or more probiotic microorganisms, a carrier which will function to transport the one or more probiotic microorganisms to the large bowel or other regions of the gastrointestinal tract of an animal, the carrier comprising a modified or unmodified resistant starch or mixtures thereof, which carrier acts as a growth or maintenance medium for microorganisms in the large bowel or other regions of the gastrointestinal tract, and an oligosaccharide. Method of increasing the number of probiotic or resident microorganisms in the gastrointestinal tract of an animal comprising providing to the animal the probiotic composition.

13 Claims, 2 Drawing Sheets

ENHANCEMENT OF MICROBIAL COLONISATION OF THE GASTROINTESTINAL TRACT

FIELD OF THE INVENTION

This invention relates to methods of enhancing the affect of nutritional compositions, particularly compositions for the delivery and maintenance of probiotic microorganisms to and in the gastrointestinal tract, especially the large bowel of animals including humans. As used in this specification, probiotics or probiotic microorganisms are a live microbial feed supplement which beneficially affects the host animal by improving its intestinal microbial balance. This is the definition provided by R. Fuller (AFRC Institute of Food Research, Reading Laboratory, UK) in—Journal of Applied Bacteriology, 1989. 66, pp.365–378. "Probiotics in Man and Animals—A Review".

BACKGROUND ART

It is the contention of many scientists that the health and well being of people can be positively or negatively influenced by the microorganisms which inhabit the gastrointestinal tract, and in particular, the large bowel. These microorganisms, through the production of toxins, metabolic byproducts, short chain fatty acids and the like affect the physiological condition and health of the host.

The constitution and quantity of the gut microflora can be influenced by conditions or stress induced by disease, life style, travel, and other factors. If microorganisms which positively affect the health and well being of the individual can be encouraged to populate the large bowel, this should improve the physiological well being of that individual.

The introduction of beneficial microorganisms, or probiotics, is normally accomplished by the ingestion of the microorganisms in drinks, yoghurts, capsules, and other forms in such a way that the organism arrives in a viable condition in the large bowel. It has been demonstrated by Englyst H. N. et al (1987) "Polysaccharides breakdown by mixed populations of human faecal bacteria", FEMS Microbiology Ecol 95: 163–71, that the bacterial fermentation of resistant starch in the large bowel produces elevated levels of short chain fatty acids, particularly beneficial types such as propionate and butyrate.

The present inventors have realised that it would be desirable to not only deliver probiotic microorganisms to the large bowel but also to provide a medium that would function to promote the growth of the microorganisms when they reach the large bowel. Surprisingly, it has been found that modified or unmodified resistant starches may function both as a means to transport the probiotic microorganisms to the large bowel and as a growth medium for the microorganism delivered to the target region of the large bowel. International publication number WO 96/08261 discloses such probiotic compositions and the content of which is incorporated into this specification for the purposes of convenient cross-reference.

It would be advantageous to further increase the numbers and/or survival in the gastrointestinal tract of probiotic microogansims provided to an animal or human so as to enhance the beneficial effect of these compositions. The present inventors have now developed improved probiotic compositions and methods of delivering probiotic microorganisms to the gastrointestinal tract of animals including humans.

DISCLOSURE OF INVENTION

In a first aspect, the present invention consists in a probiotic composition including one or more probiotic microorganisms, a carrier which will function to transport the one or more probiotic microorganisms to the large bowel or other regions of the gastrointestinal tract, the carrier comprising a modified or unmodified resistant starch or mixtures thereof, which carrier acts as a growth or maintenance medium for microorganisms in the large bowel or other regions of the gastrointestinal tract, and an oligosaccharide.

In a second aspect, the present invention consists in a method of increasing the number of probiotic or resident microorganisms in the gastrointestinal tract of an animal, the method comprising providing to the animal a probiotic composition including one or more probiotic microorganisms, a carrier which will function to transport the one or more probiotic microorganisms to the large bowel or other regions of the gastrointestinal tract, the carrier comprising a modified or unmodified resistant starch or mixtures thereof, which carrier acts as a growth or maintenance medium for microorganisms in the large bowel or other regions of the gastrointestinal tract, and an oligosaccharide.

It will be appreciated that the present invention is suitable for any animal which can benefit from probiotic treatment or administration. The present invention is particularly suitable for use in humans.

In one broad aspect, the resistant starch functions as a carrier to transport the probiotic microorganisms to the large bowel. The introduction of those microorganisms into the large bowel is beneficial as previously explained. In addition, the resistant starch, when present in the large bowel, will function as a nutritional source for microorganisms already present in the large bowel. The addition of an oligosaccharide to probiotic compositions has the surprising effect of causing an increase and persistence in the number of probiotic microorganisms in the gastrointestinal tract.

Some probiotic microorganisms may be selected such that they are able to utilise the resistant starch as a nutritional source. Thus the resistant starch will function both as a carrier and a nutritional source for those probiotic microorganisms.

There are a variety of probiotic microorganisms which are suitable for use in this invention including yeasts such as Saccharomyces, and bacteria such as the genera Bifidobacterium, Bacteroides, Clostridium, Fusobacterium, Propionibacterium, Streptococcus, Enterococcus, Lactococcus, Staphylococcus, Peptostreptococcus and Lactobacillus. The invention is not, however, limited to these particular microorganisms. The person skilled in the art would understand and recognise those microorganisms which may be included in the compositions of the invention.

In a preferred form, the probiotic microorganism is Bifidobacterium.

Typical concentration range of probiotic microorganisms administered is $10^3$ to $10^{13}$ cells per day. Usually, about $10^8$ cells per day are used in probiotic administration.

When administering probiotic compositions, typical consumption rates are about 0.1 to 10 g per kg body weight. Consumption of around 1 g per kg body weight has been found to be suitable.

Oligosaccharides suitable for the present invention may include any oligosaccharides available for consumption. Commercial oligosaccharides presently available include fructo-, galacto-, malto-, isomalto-, gentio-, xylo-, palatinose-, soybean- (includes raffinose and stachyose), chito-, agaro-, neoagaro-, α-gluco-, β-gluco-, cyclo-inulo-, glycosylsucrose, lactulose, lactosucrose and xylsucrose. It will be appreciated by one skilled in the art, however, that other oligosaccharides would also be suitable for inclusion in the composition of the present invention.

One preferred oligosaccharide suitable for the present invention is fructo-oligosaccharide (Raftilose). It will be appreciated, however, that although this particular oligosaccharide was found to be suitable in experiments carried out by the present inventors, other oligosaccharides would also be expected to have similar beneficial effects in probiotic compositions.

The oligosaccharide can be used in the composition in concentrations of about 0.01 to 10% (w/w). Preferably the concentration of oligosaccharide is about 0.05 to 5%. It has been found that between 0.1% to 1% (w/w) has the desired beneficial effect in the compositions according to the present invention.

One important effect of the present invention is that the combination of probiotic microorganism and resistant starch with the oligosaccharide results in a synergistic enhancement of the beneficial effect of delivered microorganisms when compared with probiotic composition without the oligosaccharide. This result is surprising and unexpected and therefore the present invention provides an important improvement over current probiotic compositions and methods of delivering probiotic microorganisms to the gastrointestinal tract.

As used in this specification, "resistant starch" includes those forms defined as RS1, RS2, RS3 and RS4 as defined in Brown, McNaught and Moloney (1995) Food Australia 47: 272–275. Either modified or unmodified resistant starches or mixtures thereof are used in this invention. The advantage of resistant starch in a probiotic composition is that it is largely not degraded until it reaches the large bowel. Therefore it provides a readily available substrate for fermentation by the probiotic microorganisms as soon as they arrive in the large bowel. In both cases, a preferred form of resistant starch is a high amylose starch particularly high amylose starches as disclosed and taught in WO 94/03049 and WO 94/14342, the contents of which are incorporated into this specification for the purposes of convenient cross-reference.

In WO 94/03049 and WO 94/14342, high amylose starches are disclosed which are resistant starches and include maize starch having an amylose content of 50% w/w or more, particularly 80% w/w or more, rice and wheat starch having an amylose content of 27% w/w or more and; particular granular size ranges of starches having an amylose content of 50% or more and enhanced resistant starch content, these starches including maize, barley, wheat and legumes. This invention is not, however, limited to these forms of resistant starch. For example, other forms of resistant starch derived from sources such as bananas or other fruit types, tubers such as potatoes, and mixtures or combinations thereof would be suitable for the present invention.

The compositions used in the invention may be prepared such that probiotic microorganisms, carrier and oligosaccharide are presented in combination. Alternatively, the probiotic microorganism and the carrier may be presented in each of two separate parts. In this form, either the part containing the probiotic microorganisms or the part containing the carrier and oligosaccharide may be consumed first, followed by the other part shortly thereafter. Similarly, the probiotic microorganism and the carrier may be presented in one part and the oligosaccharide in the other part. In this form, the part containing the probiotic microorganism and the carrier may be consumed first, followed by the other part shortly thereafter. It will be appreciated that the parts may be administered in the reverse order as that given above.

In an unmodified form, the resistant starch will serve as a substrate for fermentation by the probiotic microorganisms when the composition reaches the large bowel.

It may be advantageous to also chemically modify the starch to, for instance, alter the charge density or hydrophobicity of the granule and/or granule surface to enhance the attachment compatibility between the microorganism and the resistant starch. Chemical modifications, such as etherification, esterification, acidification and the like are well known in this art as being suitable chemical treatments. Similarly, other modifications can be induced physically, enzymically or by other means well known to those skilled in the art.

It may also be useful to modify the degree of enzyme susceptibility of the resistant starch by altering the conformation or structure of the starch. Examples include acid or enzyme thinning and cross bonding using difunctional reagents.

Modification of the starch may also be carried out by crystallisation. Such methods are known to the art and would be suitable for the present invention.

As used herein, Hi-maize™ (trade mark) refers to a high amylose starch obtained from Starch Australasia Limited.

In order that the present invention may be more clearly understood, preferred forms will be described with reference to the following figures and examples.

MODES FOR CARRYING OUT THE INVENTION

Methodology

TABLE 1

Pig diet formulation

Figure 1:
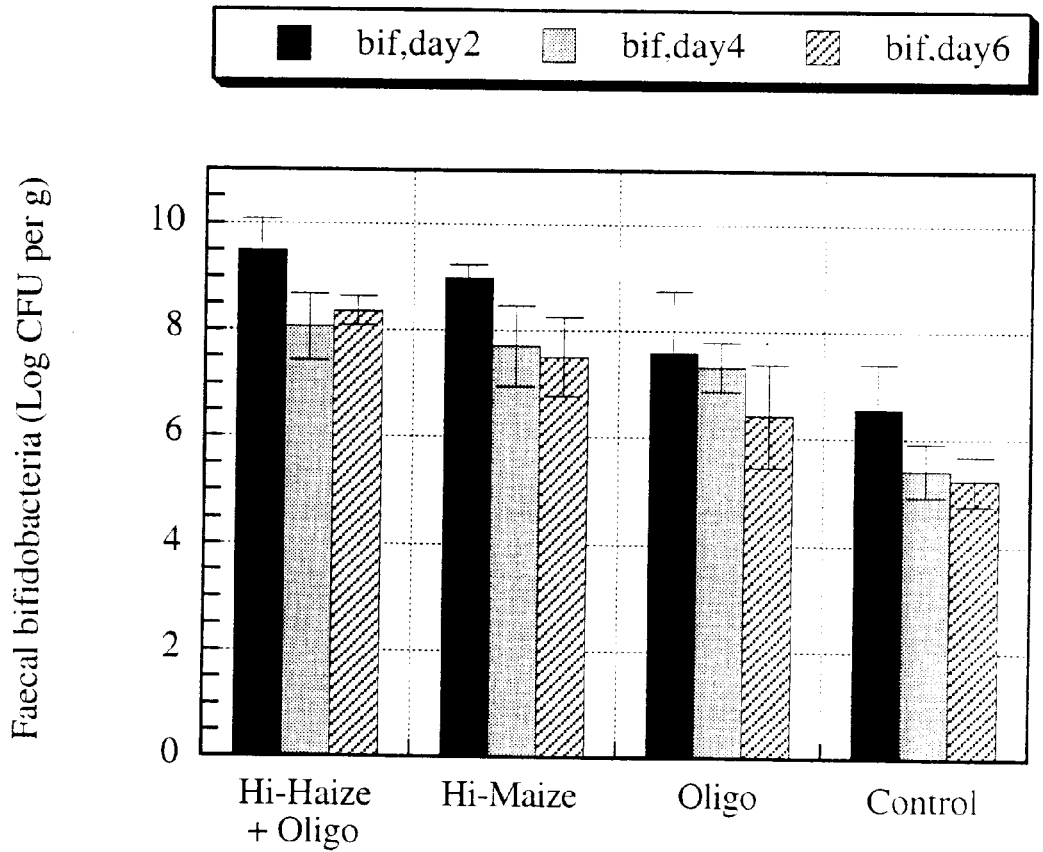
FIG. 1 shows persistance of bifidobacteria after cessation of dosage of the probiotic bifidobacteria in experimental animals and continuation of the Hi-maize™+fructo-oligosaccharide diet.

| DIET FORMULATION | g/Kg | |
|---|---|---|
| | Diet 1 & 2 | Diet 3 & 4 |
| Casein | 160 | 160 |
| Maize starch | 498 | — |
| Hi-maize ™ starch | — | 493 |
| Sucrose | 100 | 100 |
| Safflower Oil | 40 | 40 |
| Wheatbran (Laucka) | 200 | 200 |
| Vitamin/Minerals | 2 | 2 |

Sixteen pigs were divided into four groups of four pigs for the experiment. All will be their own control and have time on each diet. Pigs were fed experimental diet for a week and then had a cleaning out period of a week where they were fed pellets containing Oliquindox. Experimental feeding commenced every second Saturday, and pigs were fed twice a day. Probiotic (*Bifidobacterium longum* 1941) was fed with all meals to all pigs. Pigs on Diets 2 and 4 were fed fructo-oligosaccharide (Raftilose). After final week of feeding all animals remained on experimental diet for a further seven days but not fed Probiotic.
Formula for amounts fed to pigs: 70 g×(Body Weight)
Probiotics fed at: 0.5 g/kg body weight
Fructo-oligosaccharide: 1 g/kg body weight
Sampling:

| | |
|---|---|
| Total faecal output | Weigh total faecal output daily from Monday to Saturday morning 9 am and accurately record with time collected. |
| VFA | Take a sample of fresh faeces on Wednesday, Thursday and Friday after each morning feed. Accurately weigh out 1.5–2.0 g into a 10 ml plastic centrifuge tube and dilute 3 fold with internal standard (3.52 mM Oananthic Acid pH 7.0) Centrifuge and decant. |
| pH | Measure faecal pH after dilution with VFA internal standard. Wednesday, Thursday and Friday. |
| Faecal moisture | Freeze dry a weighed sample of faeces from each animal on Thursday. |
| Bile acids and Neutral Sterols | Collect and pool all faeces from Wednesday to Saturday morning and air dry over the weekend. Homogenise and freeze dry a sample on the following Monday. |
| Bacteria | Fresh faecal samples to be taken at the beginning of the experiment and at each clean out stage to establish level of naturally occurring or residual Bifidobacterium, each Thursday directly after the morning feed. Fresh faecal samples to be taken at each experimental stage on Thursday and Friday directly after the morning feed. At the termination of the experiment, animals were sacrificed and the proximal, mid and distal colon contents sampled for bacterial and VFA analysis. |

All pigs were weighed on Tuesday and Friday mornings before feeding.

Results

As presented in Table 2, it can be seen that the number of bifidobacteria in animals dosed with Hi-maize™ plus oligosaccharide plus bifidobacteria ($1.38 \times 10^9$ CFU/g) is twice as high as the number of bifidobacteria in animals dosed Hi-maize™+bifidobacteria ($7.24 \times 10^8$ CFU/g)and approximately 10 fold higher than those dosed oligosaccharide+bifidobacteria ($1.9 \times 10^8$ CFU/g). Control animals receiving maize had $5.5 \times 10^7$ CFU/g bifidobacteria.

TABLE 2

Number of viable bifidobacterial counts from faecal samples from 16 pigs fed either of the four experimental diets in conjunction with freeze dried *Bif. longum* 1941 over a 7 day period (CFU/g)

| | Maize | Maize/Fructo | Hi-maize ™ | Hi-maize ™/ Fructo |
|---|---|---|---|---|
| Bifidobacterium count | $5.5 \times 10^7$ | $1.9 \times 10^8$ | $7.24 \times 10^8$ | $1.38 \times 10^9$ |

Experiments were carried out in an in vitro study of human faecal homogenates. The experimental design involved incubating human faecal homogenates diluted in Wilkin Chalgren's broth (1:1000 wt/vol) with Hi-maize™ (0.5% or 1%) in the absence or presence of oligosaccharide (0.5% or 1%) and Bifidobacterium strain X8AT1 (1% inoculum). After 6 hours of anaerobic incubation at 37° C. the pH values of the different cultures were measured and the pH adjusted to 6.5. Cultures were then incubated for an additional six hours. The pH values are shown in Table 3 and the numbers of Bifidobacterium in FIG. 2. Table 4 shows the statistical analysis of the results shown in FIG. 2.

Both pH values and counts of bifidobacterium show that there is a synergistic effect when Hi-maize™ (0.5%) and fructo-oligosaccharide (0.5%) are included together in the mix. Values for this combination were greater than when 1% Hi-maize™ or 1% fructo-oligosaccharide are used singularly. Furthermore, the specific growth rate was greater for growth in the Hi-maize™ (0.5%) and fructo-oligosaccharide (0.5%) mix than in Hi-maize™ alone or fructo-oligosaccharide alone.

TABLE 3 pH values in cultures demonstrating synergistic effect of oligosaccaride in probiotic composition

| Carbon sources + inocula | 6 hours | 12 hours |
|---|---|---|
| 0.5% Raftilose + faecal slurries + X8AT1 | 5.59 | 6.03 |
| 0.5% Hi-maize ™ + faecal slurries + X8AT1 | 6.04 | 6.36 |
| 0.5% Hi-maize ™ + 0.5% Raftilose + faecal slurries + X8AT1 | 4.95 | 5.47 |
| 1% Hi-maize ™ + faecal slurries + X8AT1 | 5.5 | 5.74 |
| 1% Raftilose + faecal slurries + X8AT1 | 4.62 | 5.68 |

TABLE 4

Figure 2:
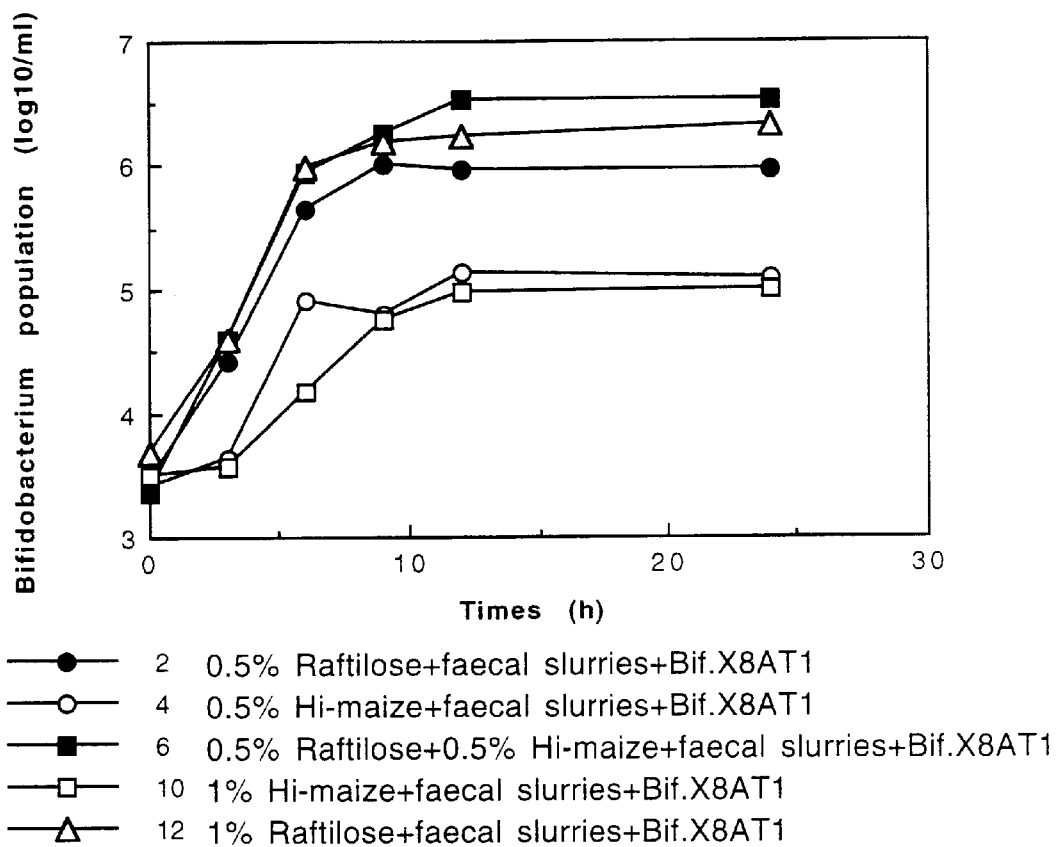
FIG. 2 shows bifidobacterial counts in human faecal slurry cultures dosed with bifidobacteria Z8AT1, Hi-maize™+fructo-oligosaccharide.

Statistical analysis of results of bifidobacterial numbers in faecal cultures shown in FIG. 2

| Group | Culture | Bifidobacterium CFU/ml | Significance* |
|---|---|---|---|
| 1 | 0.5% Raftilose + faecal slurries + X8AT1 | 5.96 ± 0.02 | 99% |
| 2 | 0.5% Hi-maize ™ + faecal slurries + X8AT1 | 5.11 ± 0.10 | 99% |
| 3 | 0.5% Raftilose + 0.5% Hi-maize ™ + faecal slurries + X8AT1 | 6.51 ± 0.08 | — |
| 4 | 1% Hi-maize ™ + faecal slurries + X8AT1 | 5.14 ± 0.38 | 99% |
| 5 | 1% Raftilose + faecal slurries + X8AT1 | 6.22 ± 0.13 | 95% |

*Scheffe F-Test (compared with Group 3)

Uses

The results in FIGS. 1 and 2 show that in pigs administered oligosaccharide+Hi-maize™+bifidobacteria, high levels of bifidobacteria persisted for a greater period of time than was observed in pigs dosed with either oligosaccharide+bifidobacteria or Hi-maize™+bifidobacteria.

The present inventors have shown in a working example that the combination of oligosaccharide, resistant starch and bifidobacteria:
(a) enhance the effect of increased numbers of intestinal bifidobacteria more than the additive effect; and
(b) that the numbers persist for a longer period of time when the three components are orally dosed.

In addition to usual uses of probiotics, the combination of resistant starch+oligosaccharide+bifidobacteria resulted in extended persistence of the higher numbers of bifidobacteria after cessation of dosage. This additional use could be valuable in situations where it is not possible to have daily dosage e.g. travelling. Persistence was also observed when Hi-maize™ plus bifidobacteria were used in these animals.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A probiotic composition comprising one or more probiotic microorganisms, a carrier which will function to transport the one or more probiotic microorganisms to the large bowel or other regions of the gastrointestinal tract of an animal, the carrier comprising a modified or unmodified resistant starch or mixtures thereof, which carrier acts as a growth or maintenance medium for microorganisms in the large bowel or other regions of the gastrointestinal tract, and an oligosaccharide selected from the group consisting of fructo-, galacto-, malto-, isomalto-, gentio-, xylo-, palatinose-, soybean- (includes raffinose and stachyose), chito-, agaro-, neoagaro-, $\alpha$-gluco-, $\beta$-gluco-, cyclo-inulo-, glycosylsucrose, lactulose, lactosucrose and xylsucrose.

2. A probiotic composition according to claim 1 wherein the oligosaccharide is fructo-oligosaccharide.

3. A probiotic composition according to claim 1 wherein the probiotic microorganism is selected from yeast, bacteria, and mixtures thereof.

4. A probiotic composition according to claim 3 wherein the yeast is Saccharomyces.

5. A probiotic composition according to claim 3 wherein the bacteria are selected from the group consisting of the genera Bifidobacterium, Bacteroides, Clostridium, Fusobacterium, Propionibacterium, Streptococcus, Enterococcus, Lactococcus, Staphylococcus, Peptostreptococcus and Lactobacillus.

6. A probiotic composition according to claim 5 wherein the bacteria is Bifidobacterium.

7. A probiotic composition according to claim 1 wherein the oligosaccharide is used at a concentration of 0.01 to 10% (w/w).

8. A probiotic composition according to claim 7 wherein the oligosaccharide concentration is between 0.05 to 5% (w/w).

9. A probiotic composition according to claim 1 wherein the resistant starch is derived from maize, barley, wheat, rice or other cereals, legumes, bananas or other fruit types, potatoes, or mixtures thereof.

10. A probiotic composition according to claim 9 wherein the resistant starch is a high amylose starch having an amylose content of 50% w/w or more, or rice and wheat starch having an amylose content of 27% w/w or more.

11. A probiotic composition according to claim 10 wherein the resistant starch is a high amylose starch having an amylose content of 80% w/w or more.

12. A probiotic composition according to claim 1 wherein the resistant starch is modified physically, chemically, enzymatically, cross-bonded using difunctional reagents, or by crystallisation.

13. A method of increasing the number of probiotic or resident microorganisms in the gastrointestinal tract of an animal, the method comprising providing to the animal a probiotic composition according to claim 1.

* * * * *